(12) United States Patent
Schneider et al.

(10) Patent No.: US 11,978,976 B2
(45) Date of Patent: May 7, 2024

(54) REMOVABLE CABLE CONNECTOR

(71) Applicant: BFLY Operations, Inc., Guilford, CT (US)

(72) Inventors: Robert Schneider, Killingworth, CT (US); Adam Mekeel Mack, Half Moon Bay, CA (US); Ryan Silvestri, Guilford, CT (US); Timothy A. Hyde, Columbia, SC (US); Jason Fischman, Stamford, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 497 days.

(21) Appl. No.: 17/362,709

(22) Filed: Jun. 29, 2021

(65) Prior Publication Data

US 2021/0408716 A1    Dec. 30, 2021

Related U.S. Application Data

(60) Provisional application No. 63/046,601, filed on Jun. 30, 2020.

(51) Int. Cl.
  *H01R 13/00* (2006.01)
  *A61B 8/00* (2006.01)
  *H01R 13/447* (2006.01)
  *H01R 13/52* (2006.01)

(52) U.S. Cl.
  CPC ......... *H01R 13/447* (2013.01); *A61B 8/4427* (2013.01); *A61B 8/56* (2013.01); *H01R 13/5224* (2013.01); *H01R 2201/12* (2013.01)

(58) Field of Classification Search
  CPC .............. H01R 13/447; H01R 13/5224; H01R 2201/12; A61B 8/4427; A61B 8/56
  See application file for complete search history.

(56) References Cited

U.S. PATENT DOCUMENTS

| 5,320,554 | A | 6/1994 | Freer et al. |
| 6,554,648 | B2 * | 4/2003 | Shi ..................... H01R 13/6582 439/79 |
| 7,335,058 | B1 | 2/2008 | Burris et al. |
| 8,033,174 | B2 | 10/2011 | Shin et al. |

(Continued)

OTHER PUBLICATIONS

Invitation to Pay Additional Fees dated Sep. 17, 2021 in connection with International Application No. PCT/US21/39610.

(Continued)

*Primary Examiner* — Phuong Chi Thi Nguyen
(74) *Attorney, Agent, or Firm* — Osha Bergman Watanabe & Burton LLP

(57) ABSTRACT

A removable cable connector engages with an electronic device such that the removable cable connector removably yet securely attaches to the electronic device. In some embodiments, the electronic device includes a plate configured to guide an electronic plug of the removable cable connector toward an electronic receptacle of the electronic device. The plate may be further configured to include one or more locators for holding the electronic receptacle of the electronic device in place. The removable cable connector may include a molded housing formed using a two-shot overmolding process to form a first overmolded strain relief portion and a second overmolded strain relief portion which cover fasteners that fasten a face plate to the connector.

20 Claims, 15 Drawing Sheets

(56) References Cited

U.S. PATENT DOCUMENTS

| | | |
|---|---|---|
| 8,461,465 B2 | 6/2013 | Golko et al. |
| 9,601,864 B2 * | 3/2017 | Schmidt ............. H01R 13/5202 |
| 9,735,492 B2 * | 8/2017 | Shum ..................... H01R 35/04 |
| 2010/0305447 A1 | 12/2010 | Dudik et al. |
| 2011/0055447 A1 | 3/2011 | Costa |
| 2014/0342597 A1 | 11/2014 | Albert |
| 2016/0139640 A1 * | 5/2016 | Hijazi ................... G06F 1/1613 |
| | | 29/857 |
| 2017/0040745 A1 * | 2/2017 | Phillips .................... H02G 3/22 |
| 2018/0115128 A1 | 4/2018 | Choi et al. |
| 2020/0076143 A1 | 3/2020 | Reese et al. |

OTHER PUBLICATIONS

International Search Report and Written Opinion dated Dec. 9, 2021 in connection with International Application No. PCT/US21/39610.

\* cited by examiner

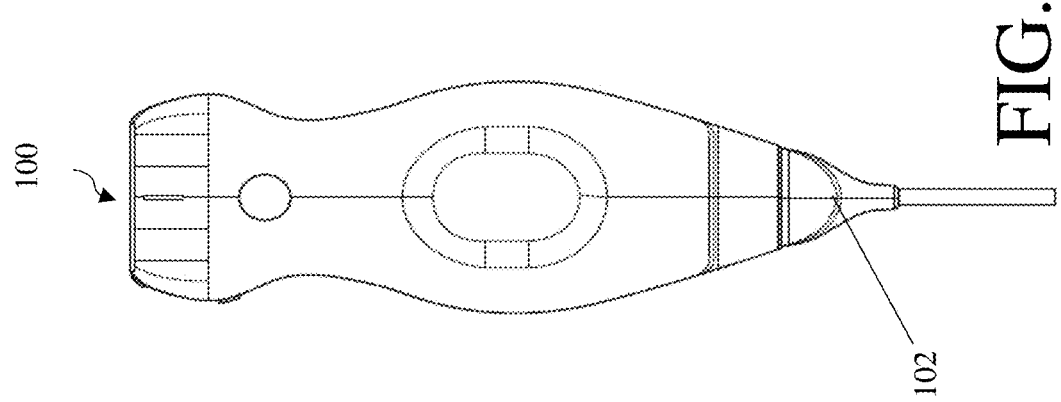
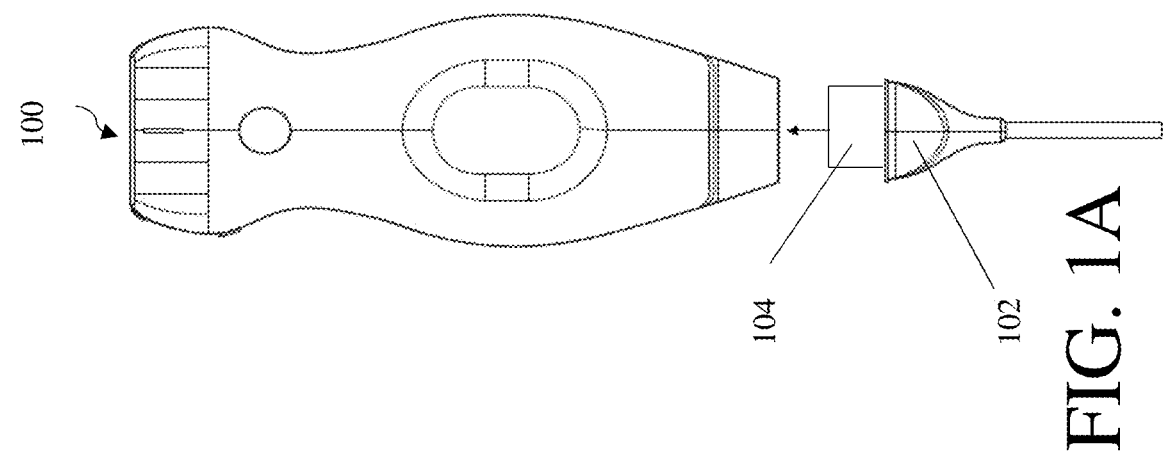
FIG. 1A
FIG. 1B

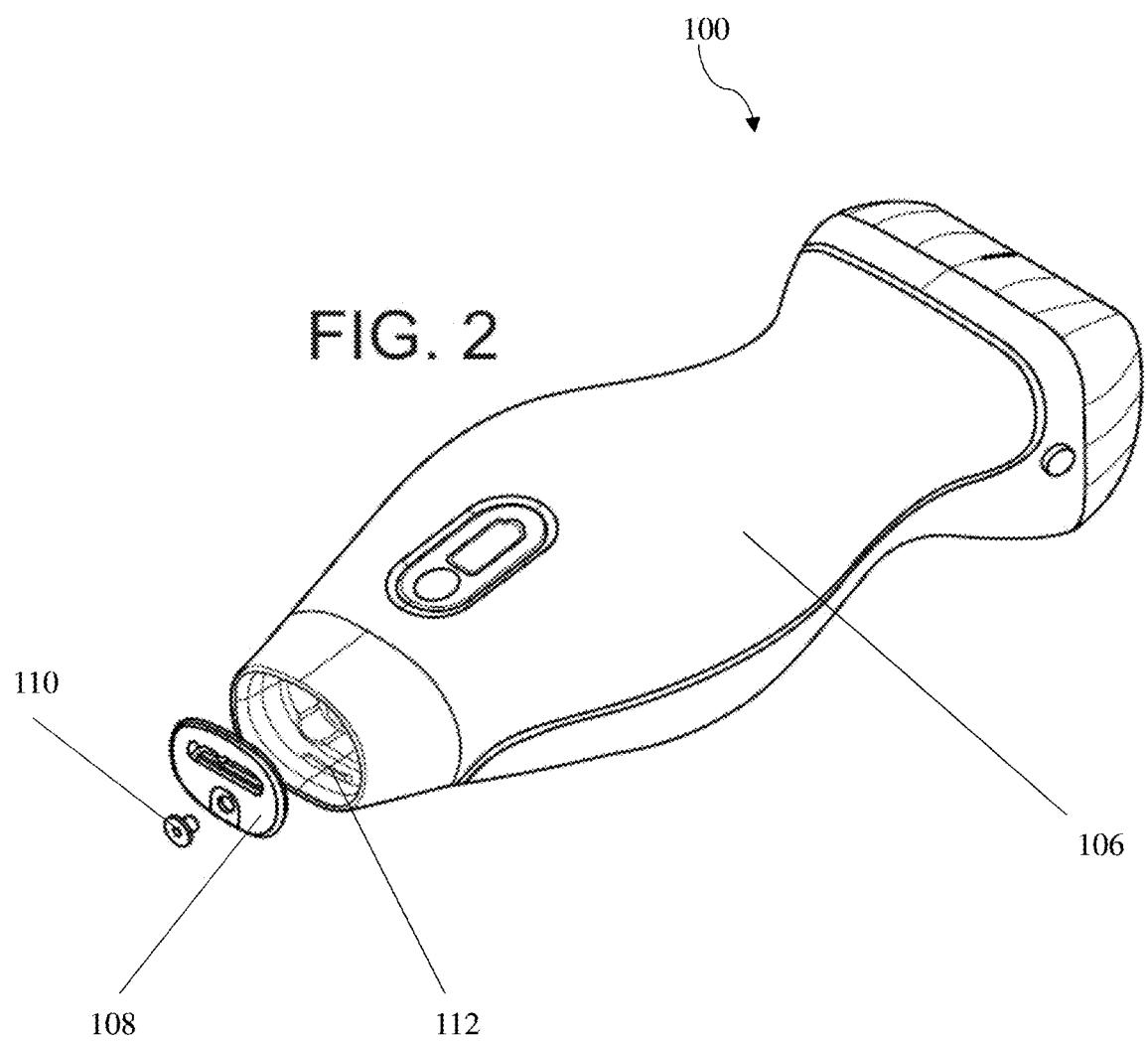

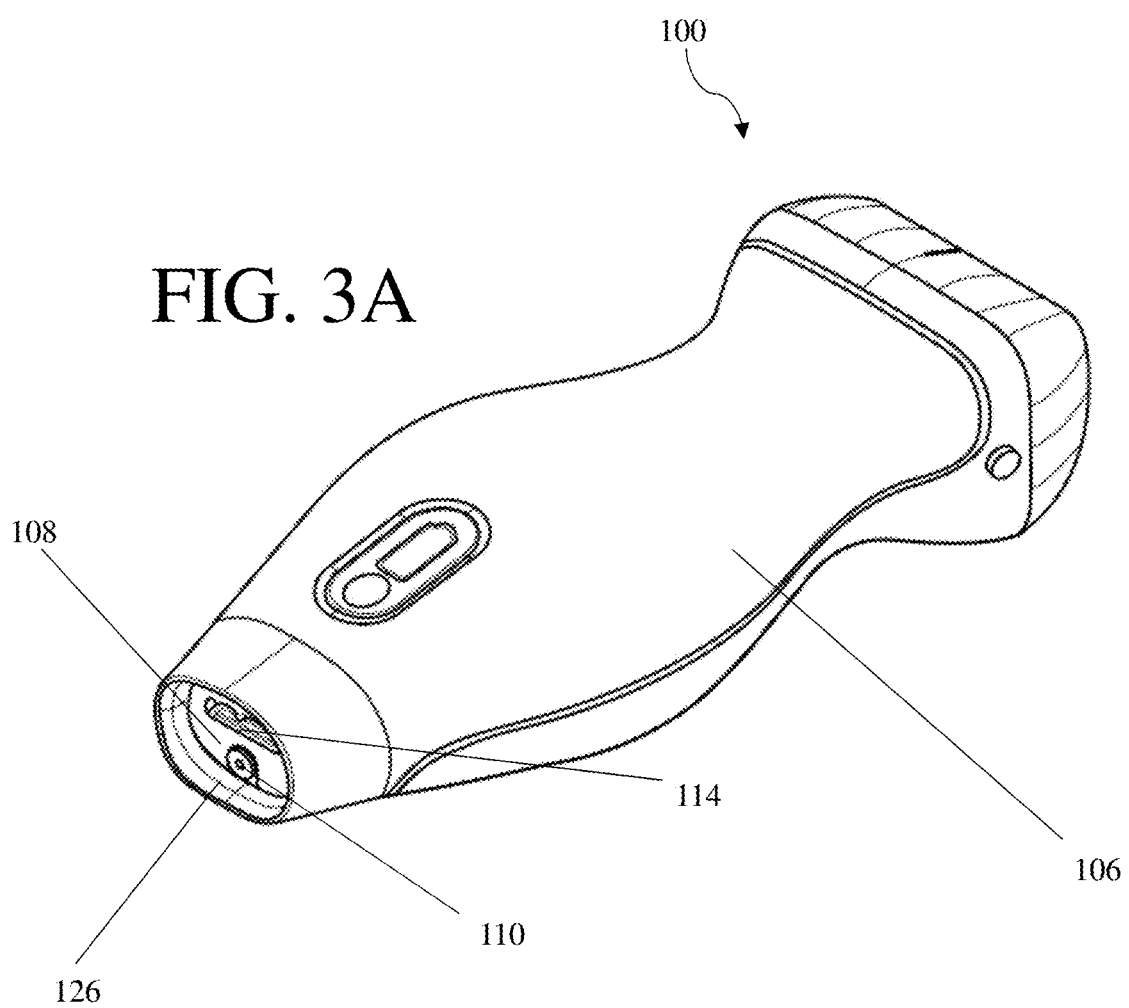

REMOVABLE CABLE CONNECTOR

CROSS-REFERENCE TO RELATED APPLICATIONS

This application claims the benefit of priority under 35 U.S.C. § 119(e) of U.S. Provisional Application Ser. No. 63/046,601, filed Jun. 30, 2020 and entitled "Removable Cable Connector," the disclosure of which is incorporated herein by reference in its entirety.

FIELD

Disclosed embodiments relate to selectively removable cable connectors, such as connectors for cables which enable electronic communication between a medical device and a mobile electronic device.

BACKGROUND

A removable cable may be used to connect an electronic device (e.g., an ultrasound probe) to another electronic device with a display, such as a mobile phone, a laptop, a PDA, a tablet, or other suitable electronic device. Typically, a cable may be removable from the electronic display device, but is fixed to the electronic device.

SUMMARY

According to one embodiment, an electronic device includes a body having a cavity at an end of the body, one of an electronic connector receptacle or a corresponding electronic connector plug being accessible via the cavity, and a plate coupled to the body, wherein the plate has one or more locators positioned on a surface facing away from the cavity, the one or more locators being configured to maintain a position the electronic connector receptacle or the electronic connector plug within the body.

According to another embodiment, an electronic device includes a body, a cavity located at a first end of the body, one or more cable connector engagement members positioned on one or more interior lateral surfaces of the cavity, and one of an electronic connector receptacle and a corresponding electronic connector plug positioned within the cavity. Further, a removable cable connector includes a housing, and the other of the electronic connector receptacle and the electronic connector plug. The other of the electronic connector receptacle and the electronic connector plug is positioned on the removable cable connector, and the removable cable connector is configured such that when the removable cable connector is inserted in the cavity, the electronic connector receptacle and the electronic connector plug connect to one another. The removable cable connector also includes one or more cavity engagement members positioned on the cable connector housing. The cavity engagement members are configured to engage with the cable connector engagement members located in the cavity of the electronic device body to releasably hold the cable connector to the electronic device body.

According to another embodiment, an electronic device includes a body, a cavity located at a first end of the body configured to receive a removable cable connector, and a plate recessed within the cavity and forming a base of the cavity. The plate has an opening through the plate, with a back side of the opening aligned with one of an electronic connector receptacle and a corresponding electronic connector plug. A removable cable connector includes a housing configured to be removably received in the cavity of the electronic device body and the other of the electronic connector receptacle and the electronic connector plug positioned on the removable cable connector. The other of the electronic connector receptacle and the electronic connector plug of the removable cable connector is configured to connect to the one of the electronic connector receptacle and the corresponding electronic connector plug. Further, a front side of the opening through the plate has a larger cross-sectional area than the back side of the opening to guide the other of the electronic connector receptacle and the electronic connector plug on the removable cable connector toward the one of the electronic connector receptacle and the corresponding electronic connector plug that is on the electronic device.

According to another embodiment, an assembly includes a connector configured to engage with a receiver of an ultrasound probe, a cable coupled to the connector, a housing enclosing at least one of a portion of the connector and a portion of the cable, a face plate attached to the housing at a front end of the connector, and at least one fastener fastening the face plate to the housing. A first strain relief portion encloses at least a portion of the housing and at least a portion of the cable, wherein the first strain relief portion extends a first distance along the cable, and a second strain relief portion. The second strain relief portion encloses at least a part of the first strain relief portion and at least a part of the cable portion. Further, the second strain relief portion extends a second distance along the cable, and the second distance is greater than the first distance. The first strain relief portion and/or the second strain relief portion cover the at least one fastener.

According to a further embodiment, a method of manufacturing includes the following steps: (1) providing an assembly including a connector configured to interface with a receiver of an ultrasound probe, a cable coupled to the connector, and a housing enclosing at least one of a portion of the connector and a portion of the cable; (2) attaching a face plate to the connector at a front end of the connector with one or more fasteners; (3) applying a first overmold to the assembly to form a first strain relief portion, wherein the first strain relief portion extends a first distance along the cable; and 4) applying a second overmold to the first strain relief portion to form a second strain relief portion, wherein the second strain relief portion extends a second distance along the cable, and wherein the second distance is greater than the first distance, and wherein at least one of the first strain relief portion and the second strain relief portion cover the one or more fasteners.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

FIG. 1A shows a removable cable being inserted into an electronic device, according to one illustrative embodiment;

FIG. 1B shows a removable cable inserted into an electronic device, according to one illustrative embodiment;

FIG. 2 is an exploded view of a plate and an electronic device, according to one illustrative embodiment;

FIG. 3A is a perspective view of the electronic device shown in FIG. 2, according to one illustrative embodiment;

DETAILED DESCRIPTION

Figure 3B:
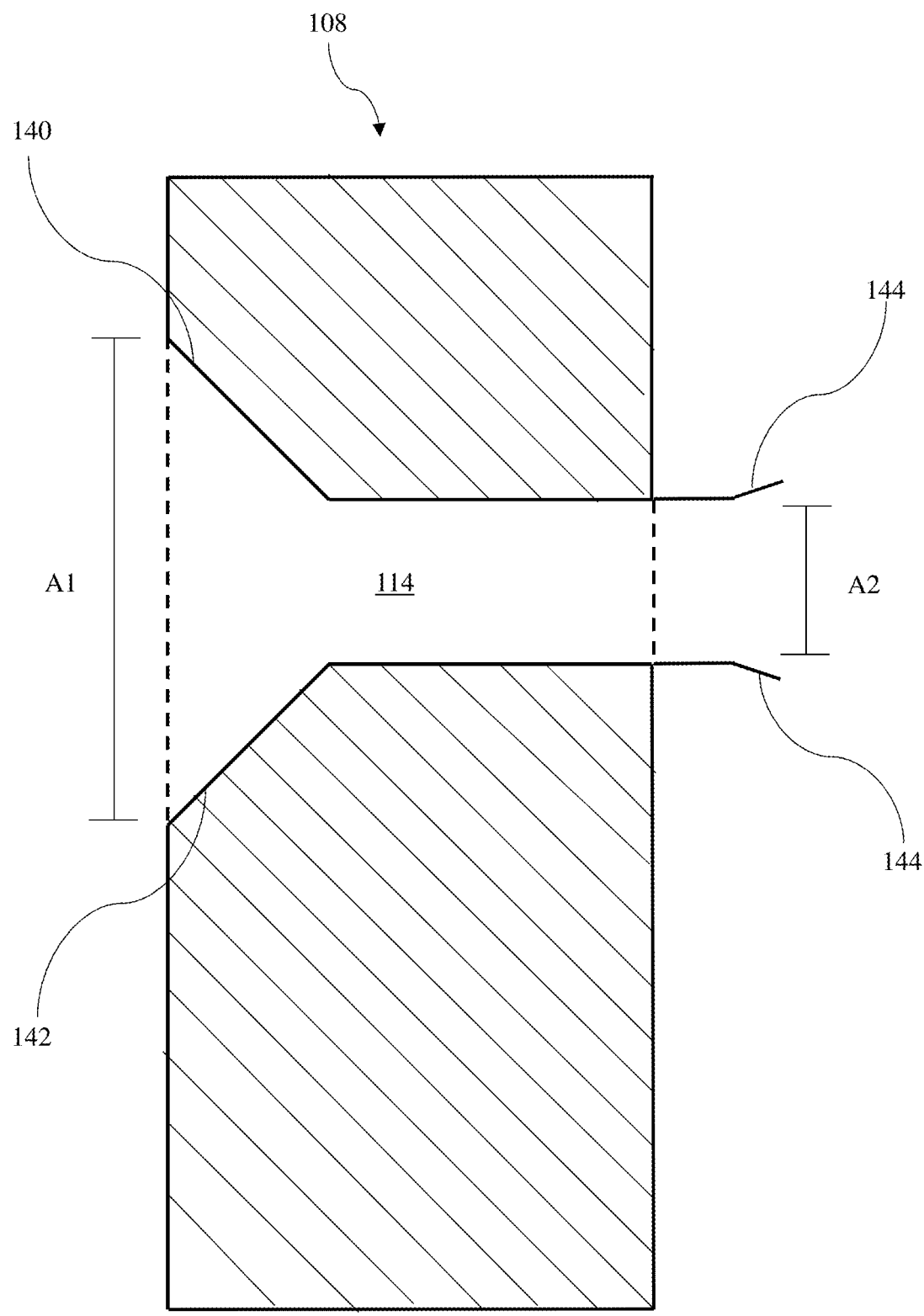
FIG. 3B is a cross-sectional view of a plate of an electronic device according to one illustrative embodiment.

An electronic device, such as an ultrasound probe, may include a cable to electronically communicate with another electronic device such as an electronic display device (e.g., a mobile phone, a laptop, a PDA, a tablet, or other suitable electronic display device). However, the electronic display device may be compatible with only a certain input/output ("I/O") port. For example, one given electronic display device may only have a lightning I/O port, while other electronic display devices may require a micro USB I/O port, a USB-C I/O port, or other suitable I/O port. However, when the electronic device includes a fixed cable, the cable may be compatible with a single type of I/O port. To allow an electronic device to be compatible with several types of I/O ports, an electronic device may include a removable cable, allowing the use of any one of a number of removable electronic cables with the electronic device, thus allowing the electronic device to communicate with a number of possible electronic display devices, each of which may be compatible with a different I/O port. However, a removable cable may come loose during use of the electronic device, interrupting the operation of the electronic device.

In view of the above, the Applicant has recognized the advantages of an electronic device that includes a removable cable capable of easily and securely engaging with an electronic device until a user purposefully disengages the cable from the electronic device. For example, it may be desirable for a removable cable to be configured to require a minimum force for removing the removable cable from the electronic device that reduces the risk of the removable cable becoming inadvertently dislodged or otherwise disengaged from the electronic device. For example, a threshold removal force may be tuned such that if the electronic device is dropped and a user catches the electronic device by grabbing the removable cable during the fall, the removable cable remains engaged with the electronic device.

Further, employing only a conventional electronic connector to connect the cable to the device may introduce certain vulnerabilities to the electronic device. For example, for some conventional electronic devices with removable cables, the point of connection between the electronic device and the removable cable may become contaminated with foreign particles, such as water or dust. Such contamination may cause the electronic device to malfunction. Further, in certain applications, such as ultrasound probes, the electronic device may come into contact with substances during use, for example a lubricant used during an ultrasound procedure.

In view of the above, the Applicant has recognized the advantages of configuring a removable cable and electronic device to prevent liquid or particles from entering the electronic device. In some embodiments, such an arrangement results in a threshold force for inserting the removable cable into the electronic device, which is higher than a force required with conventional electronic component connections. In some embodiments, an electronic device and a removable cable connector may be configured to interface with one another. The electronic cable connector may be disposed on a first end of a removable cable, while the other end of the removable cable includes a connector to interface with another electronic display device (e.g., a mobile phone, a laptop, a PDA, a tablet, or other suitable electronic display device). The electronic device may include either an electronic connector receptacle (e.g., the receiving portion of a lightning I/O port, micro USB I/O port, a USB-C I/O port, or other suitable I/O port) or a corresponding electronic connector plug (e.g., the insertion portion of a lightning I/O port, micro USB I/O port, a USB-C I/O port, or other suitable I/O port). In turn, the removable cable connector may include the other of either an electronic connector receptacle (e.g., the receiving portion of a lightning I/O port, micro USB I/O port, a USB-C I/O port, or other suitable I/O port) or a corresponding electronic connector plug (e.g., the insertion portion of a lightning I/O port, micro USB I/O port, a USB-C I/O port, or other suitable I/O port). For example, if the electronic device contains the insertion portion of an I/O port, the removable cable connector may include the receiving portion of an I/O port and vice versa.

The removable cable connector may include a housing with one or more engagement members for releasably attaching the removable cable connector to the electronic device. The electronic device also may include complementary engagement members to interface with the engagement members of the housing. Thus, the removable cable connector may be removably attached to the electronic device, for example, until a user applies a sufficient force to remove the removable cable housing from the electronic device.

The complementary engagement members of the electronic device may reside in a cavity of the electronic device, and the engagement members of the removable cable housing engage with the engagement members of the electronic device within the cavity. The removable cable housing may include a protrusion extending from the housing, and the protrusion may have a shape complementary to the cavity. The protrusion may create a seal with the cavity when the electronic device engages with the removable cable connector. The seal may serve to prevent liquids such as water or lubricant from entering the cavity. The cavity may also include a depression for interfacing with a gasket (e.g., an O-ring or other suitable gasket) of the removable cable connector housing. In some embodiments, an O-ring on the cable connector interfaces with a smooth sidewall of the cavity on the electronic device.

The electronic device may further include a plate to guide the electronic connector receptacle or corresponding electronic connector plug of the removable cable connector into the electronic connector receptacle or corresponding electronic connector plug of the electronic device. With the connection being made inside a cavity, the user may have difficulty precisely aligning the electronic connector on the cable side with the electronic connector on the device side. To facilitate connection, the bottom of the cavity may have a plate that helps guide the connector. For example, the plate may include an opening aligned with the electronic connector receptacle or corresponding electronic connector plug of the electronic device such that the electronic connector receptacle or corresponding electronic connector plug of the removable cable connector may interface with the electronic connector receptacle or corresponding electronic connector plug of the electronic device. The electronic connector receptacle or corresponding electronic connector plug of the electronic device may be positioned inwardly of the plate. On the front side (i.e., outwardly-facing side) of the plate, the opening may have a larger cross-sectional area than the cross-sectional area on the back side of the plate, and one or more slanted sidewalls may travel from the larger opening on the front side toward point of connection. As such, the plate may serve to guide the electronic connector receptacle or corresponding electronic connector plug of the removable cable connector into the complementary plug or receptacle.

To facilitate proper placement of the plate in the electronic device during manufacture and assembly, the electronic device may include a positioning rib. The plate may include an extrusion complementary to the positioning rib such that the plate interfaces with the positioning rib so that the plate may provide the guide functionality described above. Moreover, the plate may be recessed within the cavity of the electronic device to allow the removable cable connector to seal the electronic device when the removable cable connector is engaged with the electronic device as described above.

The plate may also include features, which allow the plate to hold the electronic connector receptacle or corresponding electronic connector plug of the electronic device in place. For example, the plate may include one or more locators positioned on the inner surface of the plate (i.e. a surface facing away from the cavity) to maintain the position of the electronic connector receptacle or corresponding electronic connector plug of the electronic device. The one or more locators may be a protrusion complementary to the electronic connector receptacle or corresponding electronic connector plug of the electronic device, a depression complementary to the electronic connector receptacle or corresponding electronic connector plug of the electronic device, a plurality of slanted posts complementary to the electronic connector receptacle or corresponding electronic connector plug of the electronic device, or any other suitable structure.

The housing of the removable electronic connector may include a strain relief made of two strain relief portions. The first strain relief portion may enclose at least a portion of the housing of the removable cable connector and at least a portion of the cable. Further, the first strain relief portion may extend a first distance along the cable. The second strain relief portion may enclose at least a part of the first strain relief portion and at least a part of the cable. The second strain relief portion may extend a second distance along the cable. In some embodiments, the second distance is greater than the first distance. The first strain relief portion may also include one or more apertures, such that the housing is exposed through the first strain relief portion through the one or more apertures.

A method of manufacturing the removable electronic connector is also disclosed herein. The method may include first providing an assembly including a connector configured to interface with a receiver of an ultrasound probe, a cable coupled to the connector, and a housing enclosing at least one of a portion of the connector and a portion of the cable. Next, the method may include applying a first overmold to the assembly to form a first strain relief portion, wherein the first strain relief portion extends a first distance along the cable. Then, the method may include applying a second overmold to the first strain relief portion to form a second strain relief portion, wherein the second strain relief portion extends a second distance along the cable, and wherein the second distance is greater than the first distance. The first strain relief portion may also be molded such that one or more apertures, such that the housing is exposed through the first strain relief portion through the one or more apertures.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIGS. 1A-1B show a removable cable connector 102 being connected to an electronic device 100. Electronic device 100 may accept any suitable type of removable cable connector, such as a removable cable connecter for enabling electronic communication between electronic device 100 and a mobile phone, a laptop, a PDA, a tablet, or other suitable electronic display device. Removable cable connector 102 may include a protrusion 104. Protrusion 104 may be of a shape complementary to a cavity (see FIG. 3A) of electronic device 100. In FIG. 1B, removable cable connector 102 is connected to electronic device 100. When removable cable connector 102 is connected to electronic device 100, protrusion 104 rests within the cavity of electronic device 100.

FIG. 2 is an exploded perspective view of electronic device 100. Electronic device 100 may include a body 106 and a plate 108. Body 106 may house functional components of electronic device 100 (e.g., a printed circuit board, power components, etc.). Plate 108 may be mounted within body 106 and recessed from an end of the body to form a cavity 126 within body 106. Body 106 may include a rib 112 to orient plate 108 in body 106. A fastener 110 may be used to attach plate 108 to body 106. Fastener 112 may be a screw, bolt, rivet, nail, anchor, hook, or any other suitable fastener.

FIG. 3A shows the assembled electronic device with cavity 126 configured to receive a removable cable connector. Plate 108 may include an opening 114 so as to allow an electronic connector receptacle or a corresponding electronic connector plug of a removable cable connector to interface with the electronic connector receptacle or corresponding electronic connector plug of electronic device 100.

FIG. 3B is a cross-sectional view of plate 108 according to one illustrative embodiment. In some embodiments, plate 108 may include features that guide the electronic connector receptacle or corresponding electronic connector plug of removable cable connector 102 toward the electronic connector receptacle or corresponding electronic connector plug of electronic device 100. For example, opening 114 of plate 108 may be a ramped opening. In some embodiments, opening 114 has a first cross-sectional area A1 on a first side and a second cross-sectional area A2 on a second side.

In some embodiments, a user may insert the electronic connector receptacle or corresponding electronic connector plug of removable cable connector 102 on the first side of opening 114, while the electronic connector receptacle or corresponding electronic connector plug of electronic device 100 is disposed on the second side of opening 114. Thus, the first side of opening 114 may be the outer facing side relative to body 106 of electronic device 100, and the second side of opening 114 may be the inner facing side relative to body 106 of electronic device 100. To guide the electronic connector receptacle or corresponding electronic connector plug of removable cable connector 102 to interface with the electronic connector receptacle or corresponding electronic connector plug of electronic device 100, first cross-sectional area A1 may be greater than cross-sectional area A2.

In some embodiments, the difference in cross-sectional area between the first and second sides of opening 114 creates first and second slopes 140, 142. At least a portion of the electronic connector receptacle or corresponding electronic connector plug of removable cable connector 102 may abut first and/or second slopes 140, 142 as the electronic connector receptacle or corresponding electronic connector plug of removable cable connector 102 moves toward the electronic connector receptacle or corresponding electronic connector plug of electronic device 100.

In some embodiments, plate 108 may be configured such that a user may insert the electronic connector receptacle or corresponding electronic connector plug of removable cable connector 102 on the second side of opening 114. In such embodiments, second cross-sectional area A2 is greater than first cross-sectional area A1, and cross-sectional area A2 is greater than cross-sectional area A1. Further, in such embodiments, first and second slopes 140, 142 are disposed on the second side of opening 114.

Figure 4:
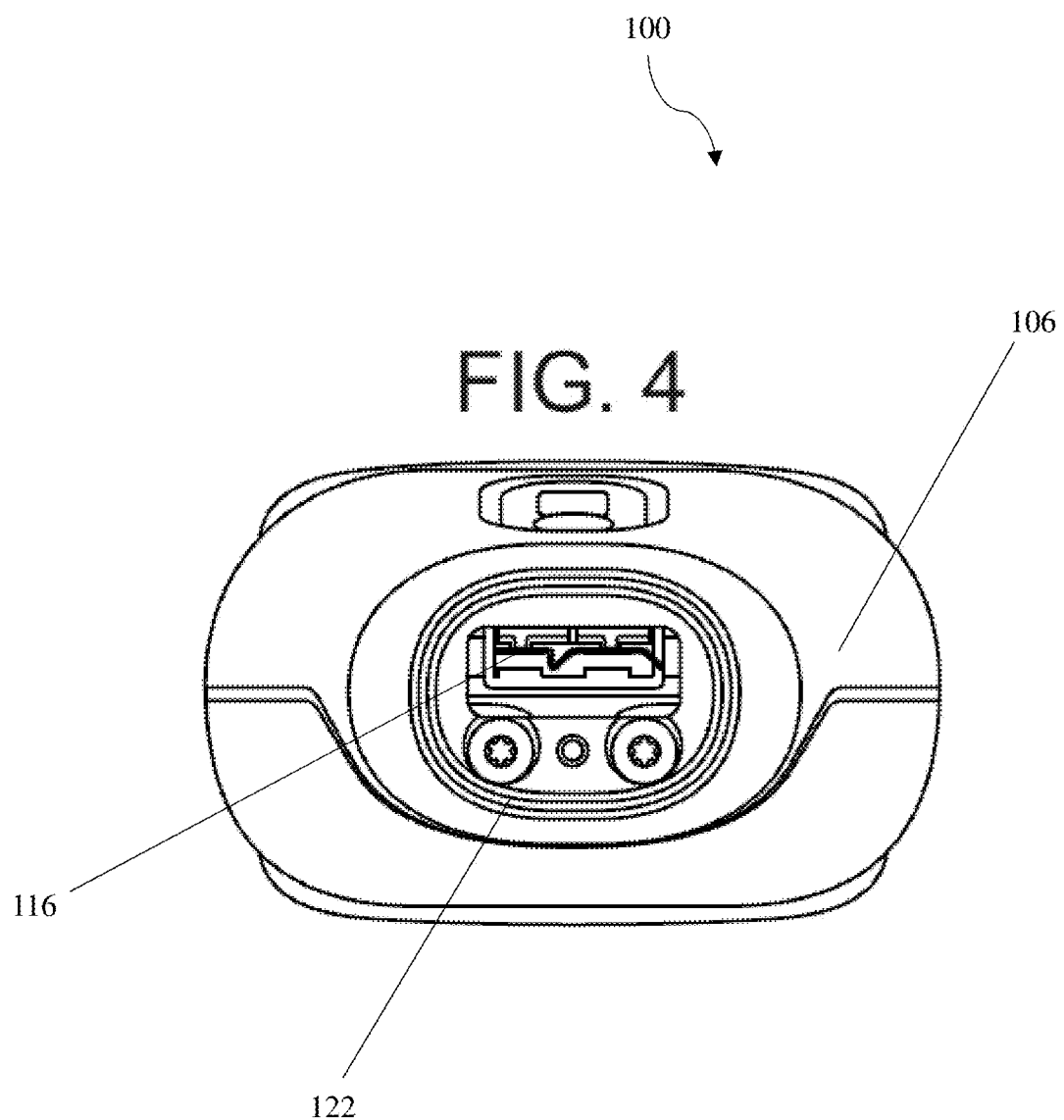
FIG. 4 is a front view of the electronic device shown in FIG. 2, according to one illustrative embodiment.

FIG. 4 is a front view of electronic device 100 with plate 108 removed. In some embodiments, body 106 houses an electronic connector receptacle 116. Electronic connector receptacle may be a receptacle for a micro-B I/O device, a receptacle for a USB-C I/O device, a receptacle for a USB-A I/O device, a receptacle for a DisplayPort I/O device, a receptacle for an HDMI I/O device, or a receptacle for any other suitable I/O device. Electronic connector receptacle 116 may be replaced with an electronic connector plug, such as a micro-B I/O device, a USB-C I/O device, a USB-A I/O device, a DisplayPort I/O device, an HDMI I/O device, or any other suitable I/O device.

Figure 5:
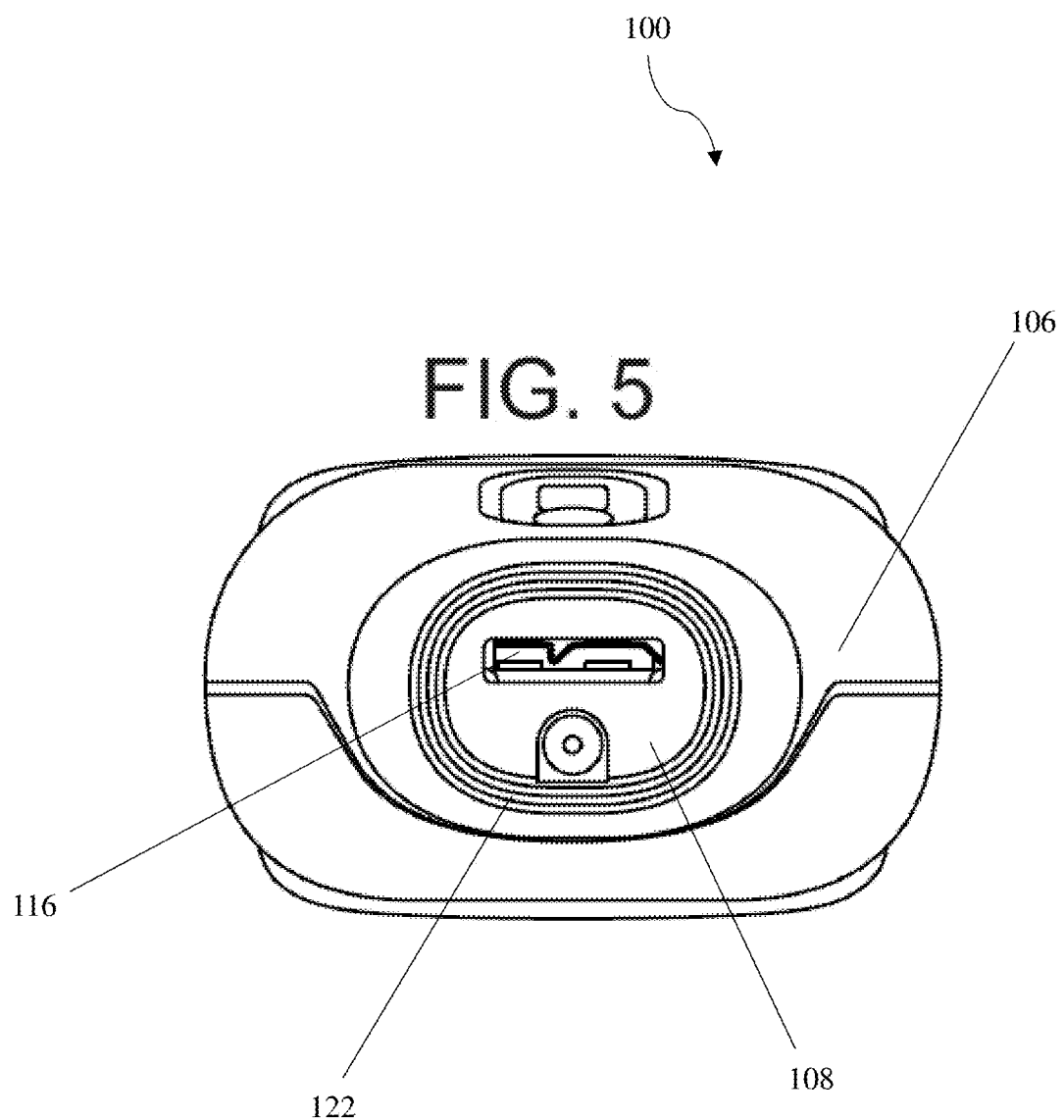
FIG. 5 is a front view of the electronic device shown in FIG. 2, according to one illustrative embodiment.
Figure 6:
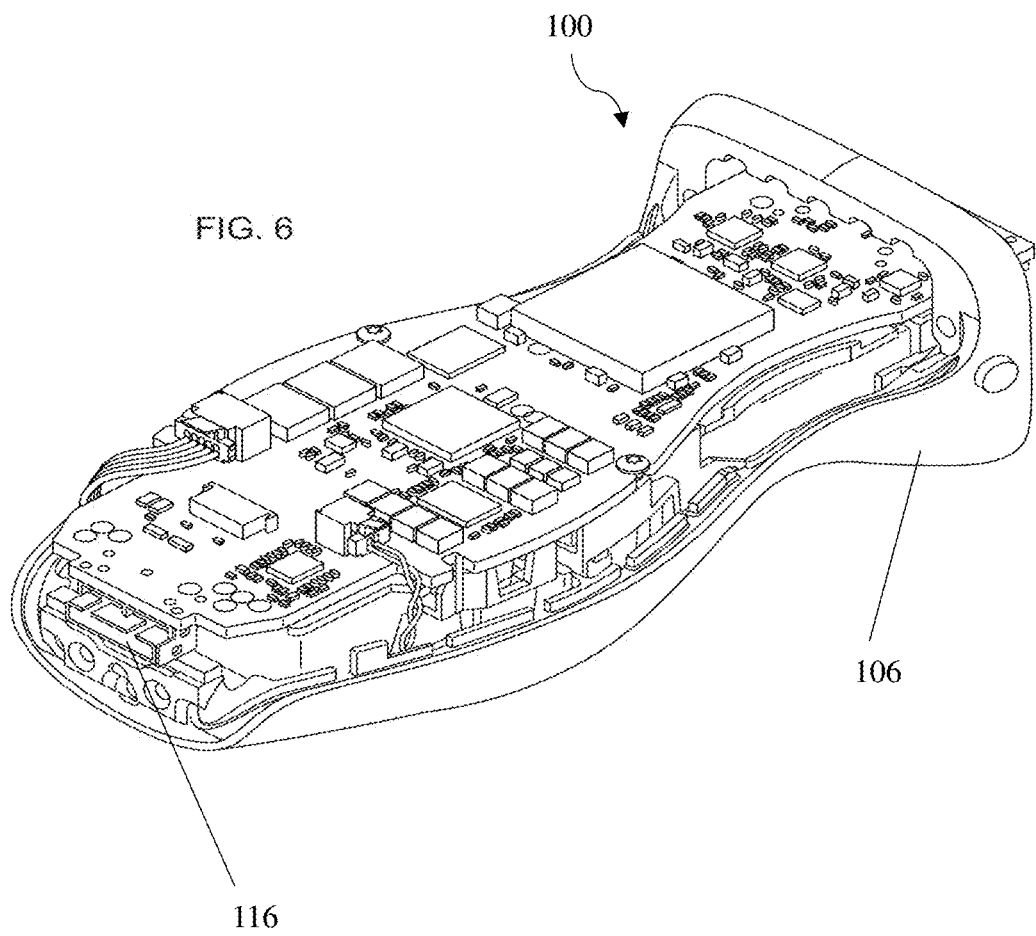
FIG. 6 is a perspective view of internal components of the electronic device shown in FIG. 2, according to one illustrative embodiment.

FIG. 5 is a front view of electronic device 100 with plate 108 installed. In some embodiments, plate 108 includes one or more features, which hold electronic connector receptacle 116 in place. For example, plate 108 may include one or more locators 144 (shown in FIG. 3B) disposed on an inwardly-facing portion of plate 108. Locators 144 may be arranged to restrain electronic connector receptacle 116 from displacement. By doing so, electronic connector receptacle may be maintained in alignment with opening 114 to facilitate connecting with the plug and/or reduce the chance of damage. For example, if a user were to forcefully push a complementary electronic connector plug into electronic connector receptacle 116 without the two components being aligned, the forces on electronic connector receptacle 116 could shear the connection of receptacle 116 off of the motherboard. One or more locators 144 may take on any suitable configuration, including one or more protrusions, one or more depressions, one or more slanted posts or any other suitable structure. Of course, the one or more locators may include combinations of different structures.

Figure 7:
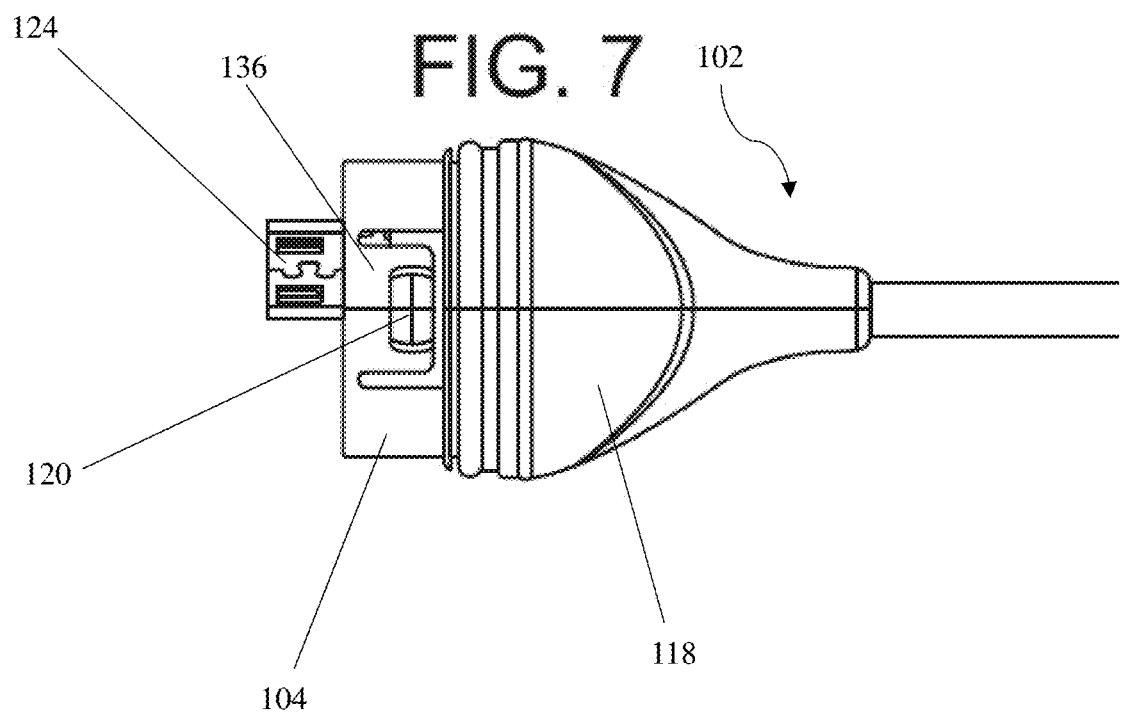
FIG. 7 is a top view of a removable cable connector according to one illustrative embodiment.
Figure 8:
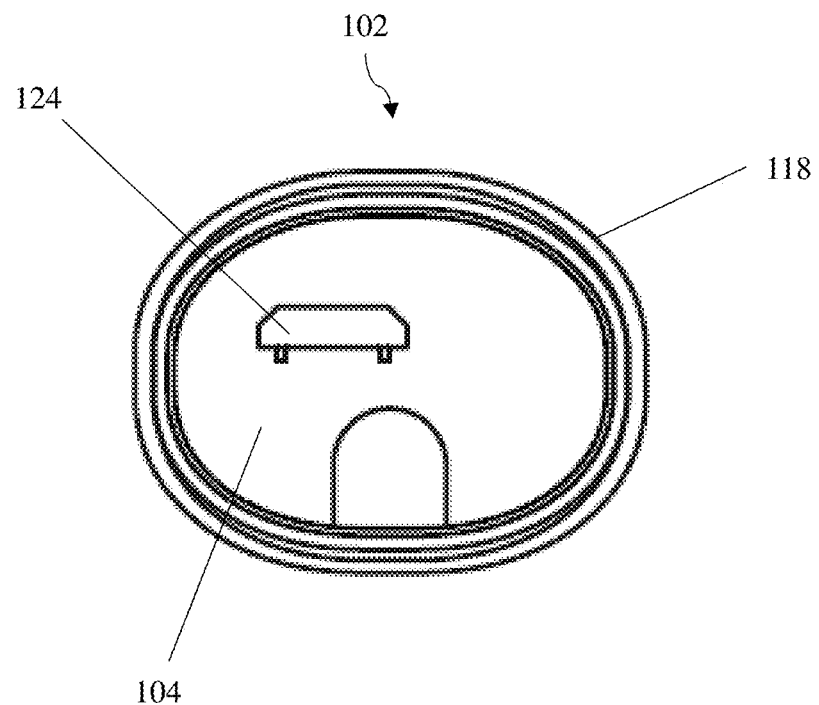
FIG. 8 is a front view of the removable cable connector shown in FIG. 7 according to one illustrative embodiment.
Figure 9:
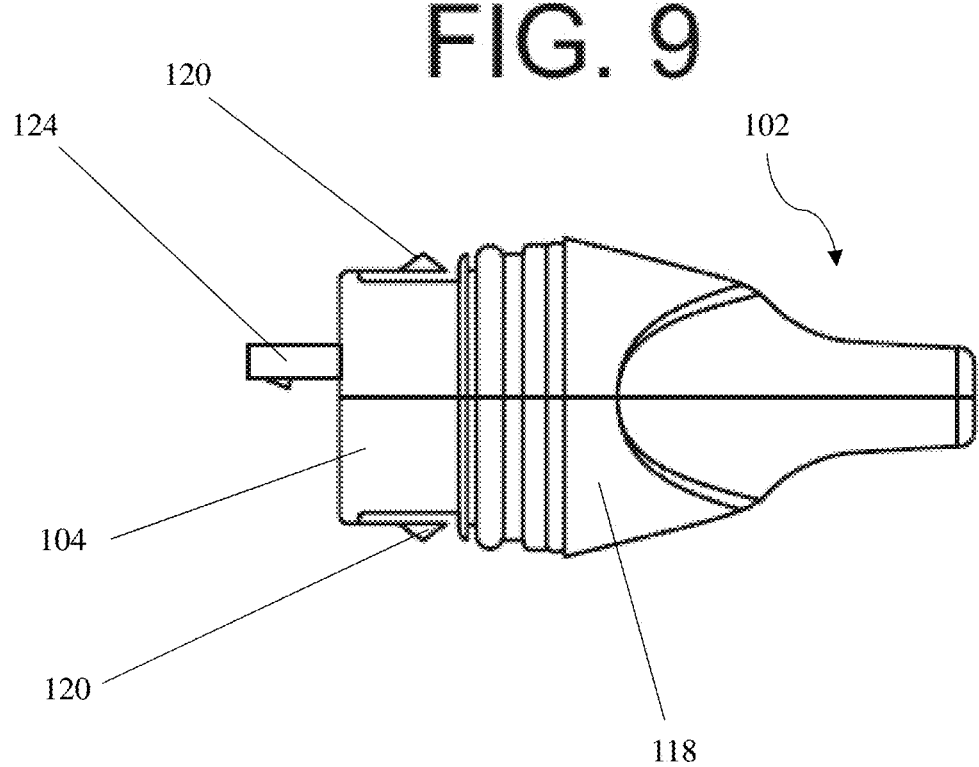
FIG. 9 is a side view of the removable cable connector shown in FIG. 7 according to one illustrative embodiment.

FIGS. 7-9 are a top, front, and side views of removable cable connector 102, respectively. In some embodiments, removable cable connector 102 includes a housing 118, a protrusion 104, an engagement member 120, and an electronic connector plug 124. Electronic connector plug 124 may interface with electronic connector receptacle 116 to enable electronic communication between electronic device 100 and removable cable connector 102. Electronic connector plug 124 may be any suitable I/O device, such as a micro-B I/O device, a USB-C I/O device, a USB-A I/O device, a DisplayPort I/O device, an HDMI I/O device, or any other suitable I/O device. Electronic connector plug 124 may instead be an electronic connector receptacle, such as a receptacle for a micro-B I/O device, a receptacle for a USB-C I/O device, a receptacle for a USB-A I/O device, a receptacle for a DisplayPort I/O device, a receptacle for an HDMI I/O device, or a receptacle for any other suitable I/O device.

Removable cable connector 102 may include features that allow removable cable connector 102 to be removably attached to electronic device 100, for example within cavity 126. For example, one or more cable connector engagement members 120 may engage with one or more corresponding cavity engagement members 122 (shown in FIGS. 4-5). One or more cable connector engagement members 120 may be disposed on protrusion 104 of removable cable connector 102. One or more cavity engagement members 122 disposed in the cavity may have a shape which is complementary to the one or more cable connector engagement members 120. For example, one or more cable engagement members 120 may extend from a surface of protrusion 104 in the shape of a triangular prism, and the cavity engagement members 122 may be recesses in the shape of a triangular prism. In some embodiments, cavity engagement members 122 may be a series of ribs or ridges within cavity 126. When removable cable connector 102 is inserted into electronic device 100, the one or more extended cable connector engagement members 120 may abut the ribbed or ridged cavity engagement members 122, preventing removable cable connector 102 from exiting cavity 126 unless a sufficiently large force is applied to removable cable connector 102. Cavity engagement members 122 need not be ribs or ridges, and cable connector engagement members 120 need not extend from protrusion 104, as cavity engagement members 122 and cable connector engagement members 120 may be configured in any suitable manner. In some embodiments, the cavity engagement members 122 may be protrusions, such as triangular prisms, and the corresponding engagement members on the removable cable connector may pass by the cavity engagement members when the connector is inserted into the cavity. The engagement members on the connector side and/or the engagement members on the cavity side may be flexible to permit the engagement members to pass one another when a force greater than an insertion threshold force is used to push the cable connector into the cavity.

Cavity engagement members 120 may be positioned on lateral portions of the cavity, such as on lateral sidewall of the cavity. Additional cavity engagement members may be positioned on a base of the cavity.

In the illustrated embodiment, cable connector engagement members 120 have a triangular cross-section, and are positioned on a living hinge 136. The shape of member 120 and the flexibility of living hinge 136 may be configured such that the threshold force sufficient for removal of the cable connector from the cavity is forty newtons in some embodiments. In other embodiments, the threshold removal force may be set at fifty newtons, sixty newtons, or seventy newtons. In some embodiments, the threshold force for removal is no more than 110 newtons. A living hinge may be employed within the cavity in addition to, or instead of, the living hinge on the cable connector.

The cable connector engagement members 120 and cavity engagement members 122 may be configured to provide a threshold insertion force in some embodiments. For example, in some embodiments, the assembly may provide a threshold force of eighty newtons such that at least eighty newtons of force needs to be applied to the cable connector to fully insert and attach the cable connector to the device. In some embodiments, the threshold insertion force is at least sixty newtons. In other embodiments, the threshold insertion force is at least seventy newtons, and in other embodiments, the threshold insertion force is at least ninety newtons. In some embodiments, the threshold insertion force is less than one hundred newtons. Any suitable threshold insertion force may be used.

Other shapes and/or arrangements of cable connector engagement members 120 and/or cavity engagement members 122 may be used, and other threshold insertion forces and threshold removal forces may result from these arrangements.

Removable cable connector 102 and electronic device 100 may be arranged to prevent external particles and liquids from entering electronic device 100 when removable cable connector is connected to electronic device 100. For example, protrusion 104 may be of a shape complementary to cavity 126. In some embodiments, protrusion 104 has a rectangular shape with rounded corners, and cavity 126 includes a similarly-shaped recess. In some embodiments, protrusion 104 and cavity may be cylindrical. When electronic connector 102 is connected with electronic device 100, sidewalls of protrusion 104 seal against sidewalls of cavity 126, preventing foreign particles from entering electronic device 100. As will be appreciated by one of skill in the art, protrusion 104 and the recess of cavity 126 need not be cylindrical or rectangular, as the cavity 126 and protrusion 104 may be any suitable shape.

Figure 10:
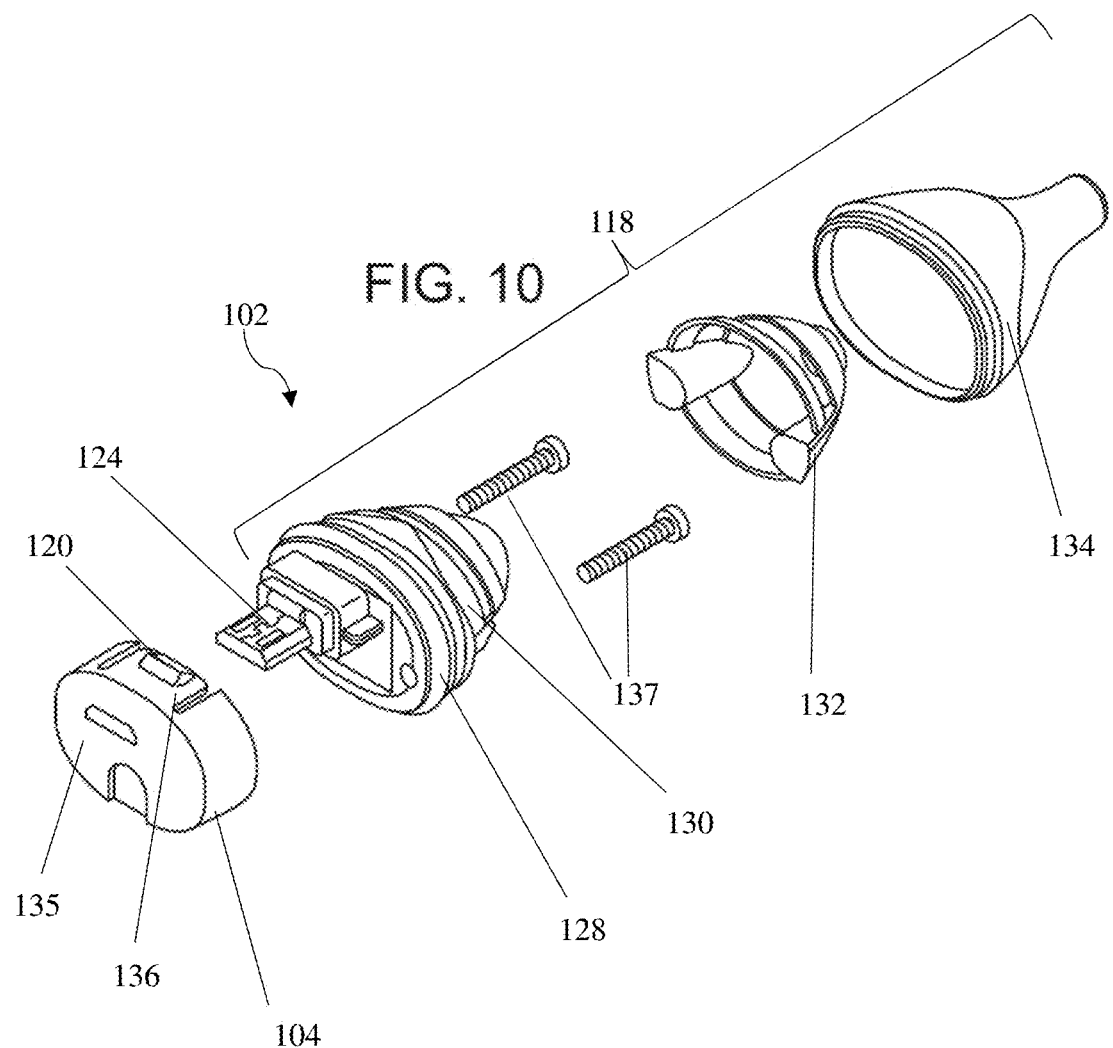
FIG. 10 is a exploded view of the removable cable connector shown in FIG. 7 according to one illustrative embodiment.

FIG. 10 is an exploded view of removable cable connector 102. Housing 118 of removable cable connector 102 may include: (1) an inner housing 130, (2) a first strain relief portion 132, and (3) a second strain relief portion 134. In some embodiments, electronic connector plug 124 is attached to inner housing 130. Inner housing 130 may also include a gasket 128. Cavity 126 may include a depression for receiving and holding gasket 128. Gasket 128 may serve to create a mechanical seal between removable cable connector 102 and electronic device 100. In some embodiments, gasket 128 is an O-ring which fits onto inner housing 130. Gasket 128 may rest within a detent in inner housing 130, be attached to inner housing 130 using an adhesive (e.g., epoxy, resin, glue, hot-melt adhesive, Polyvinyl Acetate, or other suitable adhesive), or employ any other suitable arrangement. In turn, gasket 128 may be press fit into a depression of cavity 126 when a user attaches removable cable connector 102 to electronic device 100. Gasket 128 may be configured to fill geometric irregularities between removable cable connector 102 and cavity 126 of electronic device 100. Thus, gasket 128 may seal the combination of electronic device 100 and removable cable connector 102 from foreign materials such as liquids (e.g., water, lubricant, or other liquid) and/or particles (e.g., dust, allergens, spores, or other particles). Gasket 128 may be made from Nitrile, Neoprene, Silicone, Ethylene Propylene Rubber, Polyurethane, Polytetrafluoroethylene ("PTFE"), compressed fiber, cork, or any other suitable material. In some embodiments, an O-ring may be disposed in the cavity, for example on a lateral sidewall of the cavity.

A face plate 135 may be attached to the housing 130 with one or more fasteners, such as screws 137. Once the face plate is attached with screws 137, a cable strain relief may be added to the housing. In some embodiments, the strain relief covers the screws, which may help prevent unintended removal of the screws.

Figure 11:
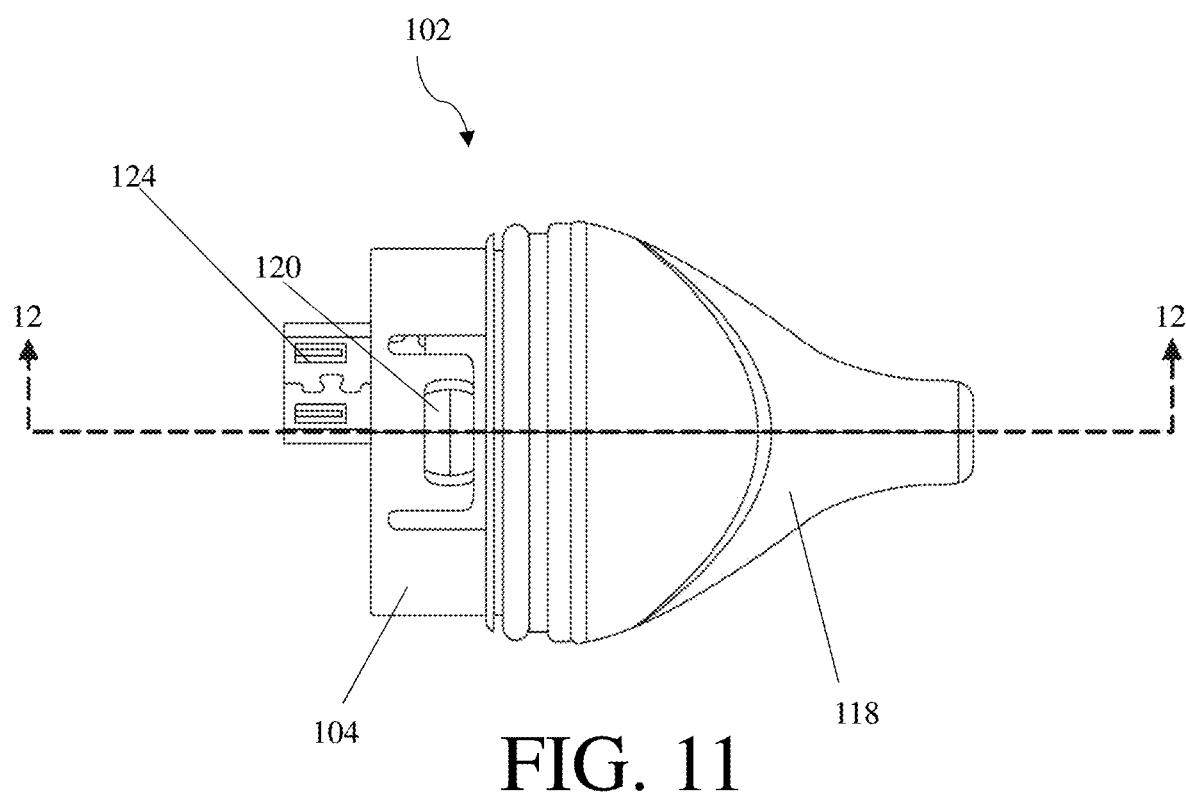
FIG. 11 is a top view of a removable cable connector according to one embodiment.
Figure 12:
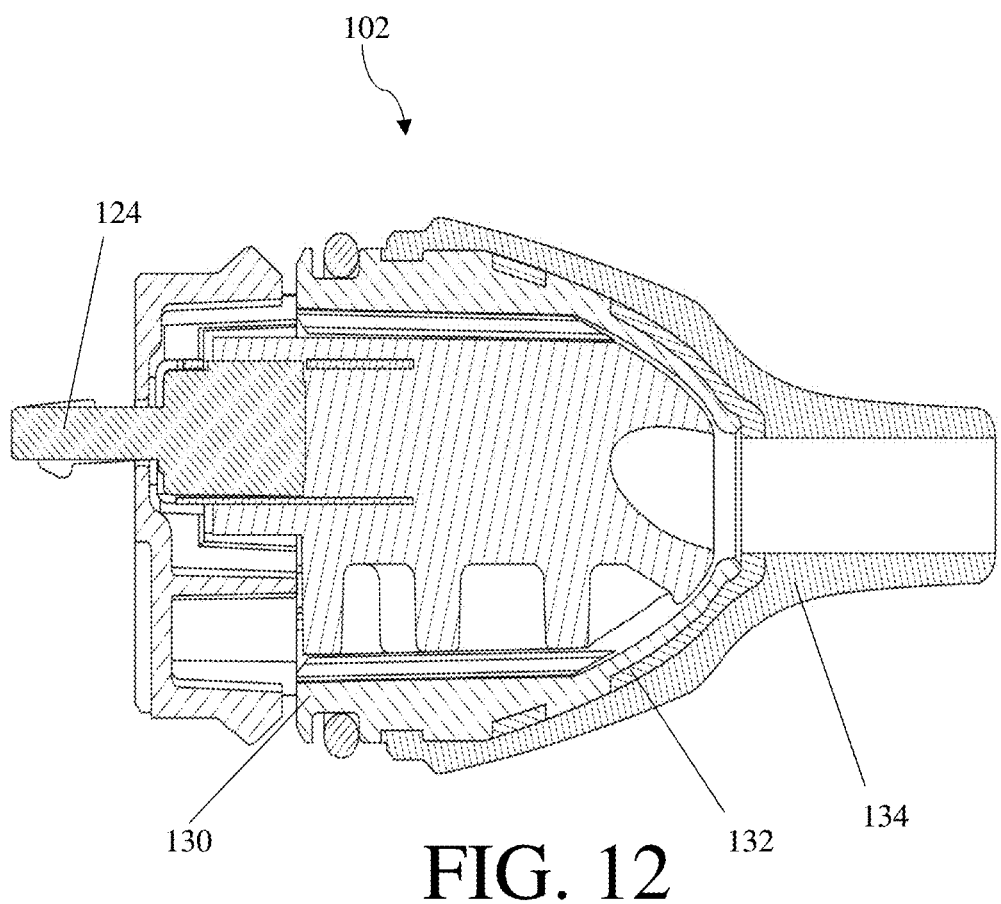
FIG. 12 is a cross-sectional view of a removable cable connector taken along line 12-12 in FIG. 11.

First strain relief portion 132 and second strain relief portion 134 may be applied to inner housing 130 during a two-shot overmolding process. In the first shot of the two-shot overmolding process, first strain relief portion 132 is molded over inner housing 130. In some embodiments, inner housing 130 may have a non-uniform, ribbed, or ridged structure. Thus, first strain relief portion 132 may include one or more apertures to accommodate the non-uniform, ribbed, or ridged structure of inner housing 130. After first strain relief portion 132 is applied to inner housing 130 during the first shot of the two shot overmolding process, second strain relief portion 134 is molded over the combination of inner housing 130 and first strain relief portion 132. Second strain relief portion 134 may serve to smoothen the surface of removable cable connector 102 and improve the aesthetic look of removable cable connector 102. FIG. 12 is a cross-sectional view of removable cable connector 102 along line 12-12 (shown in FIG. 11). As can be seen in FIG. 12, when fully assembled, first strain relief portion 132 may cover at least a portion of the inner housing 130. Further, second strain relief portion 134 may cover at least a portion inner housing 130 and first strain relief portion 132. In some embodiments, first and second strain relief portions 132, 134 also cover a portion of a cable extending from inner housing 130. In some embodiments, second strain relief portion 134 covers a greater portion of the cable than first strain relief portion 132.

By using two or more overmolding steps to construct the strain relief, a larger strain relief may be manufactured as compared to a single-shot strain relief process. Additionally, the process allows a first shot to fill in gaps between the ribs of the housing to provide a secure engagement of the strain relief to the housing, while the second shot provides a cosmetic layer to conceal the ribs of the housing. The second shot also allows a smooth and elongated portion of the strain relief to be positioned over the cable as the cable extends from the connector, thereby providing a seal between the cable and the connector in some embodiments. First and second strain relief portions 132, 134, as well as inner housing 130, may be made of a thermoplastic elastomer such as thermoplastic olefins, styrenic, vulcanized compounds, copolyester compounds, polyurethane, polyamide, or any other suitable material. Further, the materials making up first and second strain relief portions 132, 134, as well as inner housing 130, may have a durometer of greater than or equal to Shore 50A and less than or equal to Shore 70A. Of course, the materials making up first and second strain relief portions 132, 134, as well as inner housing 130 may have durometers of greater than Shore 70A or less than Shore 50A, depending on the application.

Figure 13:
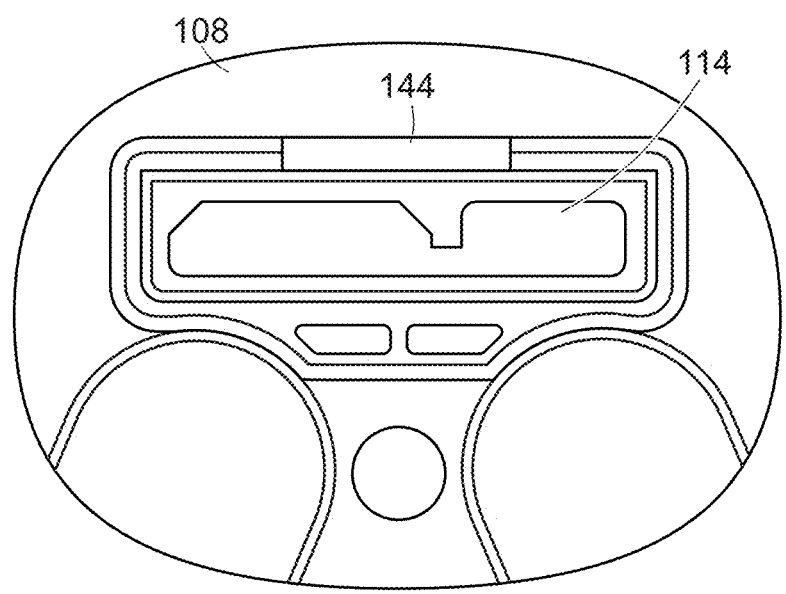
FIG. 13 is a rear view of a plate of an electronic device according to one illustrative embodiment.
Figure 14:
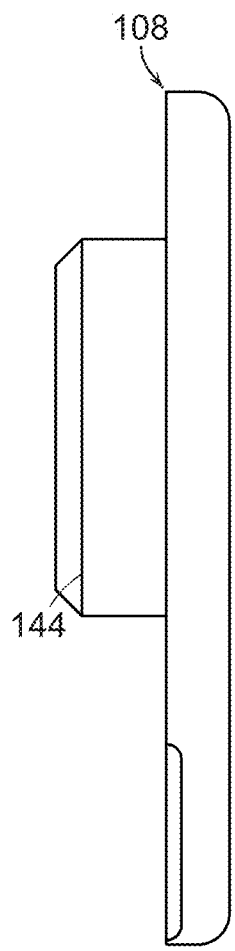
FIG. 14 is a side view of the plate shown in FIG. 13 according to one illustrative embodiment.

FIGS. 13-14 are rear and side views of plate 108 respectively. In some embodiments, plate 108 includes a single locator 144. Locator 144 may be configured to surround opening 114 and correspond to the cross-sectional shape of electronic connector receptacle 116. For example, locator 144 may be a wall that extends perpendicularly from the plate and surrounds electronic connector receptacle 116.

Locator 144 may also include grips, slants, protrusions, or any other suitable structure for holding electronic connector receptacle 116 in place, particularly when a user is inserting or removing electronic connector plug 124 from electronic connector receptacle 116. By positioning connector receptacle 116 in alignment with the plate opening, locator 144 may prevent insertion forces from a plug from pressing on the receptacle in such a way as to damage the receptacle 116 or damage the connection of the receptacle to the device.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. An electronic device comprising:
   a body having a cavity at an end of the body;
   one of an electronic connector receptacle or a corresponding electronic connector plug being accessible via the cavity;
   a plate positioned within the cavity, wherein the plate has one or more locators positioned on a surface facing away from the cavity, the one or more locators being configured to maintain a position the electronic connector receptacle or the electronic connector plug within the body.

2. The electronic device of claim 1, wherein the plate includes an opening and a front side of the opening through the plate has a larger cross-sectional area than the back side of the opening.

3. The electronic device of claim 1, wherein the cavity includes a depression configured to accept a gasket.

4. The electronic device of claim 1, wherein the one of an electronic connector receptacle or a corresponding electronic connector plug is an electronic connector receptacle.

5. The electronic device of claim 1, further comprising one or more cable connector engagement members positioned on one or more interior lateral surfaces of the cavity.

6. The electronic device of claim 1, wherein the plate forms a base of the cavity.

7. The electronic device of claim 6, wherein the cavity includes a positioning rib configured to align the plate relative to the body.

8. An electronic device and a removable cable connector comprising:
   an electronic device including:
      a body;
      a cavity located at a first end of the body;
      one or more cable connector engagement members positioned on one or more interior lateral surfaces of the cavity;
      one of an electronic connector receptacle and a corresponding electronic connector plug positioned within the cavity; and
   a removable cable connector including:
      a housing;
      the other of the electronic connector receptacle and the electronic connector plug being positioned on the removable cable connector, and the removable cable connector being configured such that when the removable cable connector is inserted in the cavity, the electronic connector receptacle and the electronic connector plug connect to one another;
      one or more cavity engagement members positioned on the cable connector housing, the cavity engagement members configured to engage with the cable connector engagement members located in the cavity of the electronic device body to releasably hold the cable connector to the electronic device body.

9. The electronic device and removable cable connector of claim 8, wherein the one or more cable connector engagement members and the one or more cavity engagement members are configured such that a threshold insertion force sufficient to insert the cable connector from the cavity is at least 40 newtons and is less than 100 newtons.

10. The electronic device and removable cable connector of claim 8, wherein the one or more cavity engagement members positioned on the cable connector housing are configured to prevent water from entering the cavity of the electronic device when the cavity engagement members are engaged with the cable connector engagement members located in the cavity of the electronic device body.

11. The electronic device and removable cable connector of claim 8, wherein the cavity has a shape complementary to the shape of a protrusion of the cable connector housing.

12. The electronic device and removable cable connector of claim 8, wherein the electronic device comprises a portable ultrasound machine.

13. The electronic device and removable cable connector of claim 8, wherein the one or more cable connector engagement members and the one or more cavity engagement members are configured such that a threshold removal force sufficient to remove the cable connector from the cavity is at least 40 newtons.

14. The electronic device and removable cable connector of claim 13, wherein the threshold force is at least 50 newtons.

15. The electronic device and removable cable connector of claim 13, wherein the threshold force is no more than 110 newtons.

16. The electronic device and removable cable connector of claim 13, wherein the one or more cable connector engagement members and the one or more cavity engagement members are configured such that a threshold insertion force sufficient to insert the cable connector from the cavity is no more than 80 newtons.

17. An electronic device and removable cable connector comprising:
   an electronic device including:
      a body;
      a cavity located at a first end of the body, the cavity being configured to receive a removable cable connector;
      a plate recessed within the cavity and forming a base of the cavity, the plate having an opening through the plate, with a back side of the opening aligned with one of an electronic connector receptacle and a corresponding electronic connector plug; and a removable cable connector including:
- a housing configured to be removably received in the cavity of the electronic device body;
- the other of the electronic connector receptacle and the electronic connector plug being positioned on the removable cable connector;
- wherein the other of the electronic connector receptacle and the electronic connector plug of the removable cable connector is configured to connect to the one of the electronic connector receptacle and the corresponding electronic connector plug;

wherein a front side of the opening through the plate has a larger cross-sectional area than a cross-sectional area of the back side of the opening to guide the other of the electronic connector receptacle and the electronic connector plug on the removable cable connector toward the one of the electronic connector receptacle and the corresponding electronic connector plug that is on the electronic device.

18. The electronic device and removable cable connector of claim 17, wherein the cavity has sidewalls with forming a shape complementary to the shape of sidewalls of a protrusion of the cable connector housing.

19. The electronic device and removable cable connector of claim 17, wherein the cavity includes a positioning rib configured to align the plate relative to the body.

20. The electronic device and removable cable connector of claim 17, wherein the plate has one or more locators positioned on a surface facing away from the cavity, the one or more locators being configured to maintain a position the electronic connector receptacle or the electronic connector plug within the body.

* * * * *